United States Patent [19]

Nagata et al.

[11] Patent Number: 5,024,731
[45] Date of Patent: Jun. 18, 1991

[54] METHOD OF MANUFACTURING MATERIAL FOR MEDICAL AND PHARMACEUTICAL PRODUCTS FROM PYROLIGNEOUS ACID

[76] Inventors: Katsumi Nagata, 10-18, Iwaidani 4-chome, Matsuyama-shi, Ehime-ken; Hisako Nagata, 2-10, Kyoyama 1-chome, Okayama-shi, Okayama-ken, both of Japan

[21] Appl. No.: 442,990

[22] Filed: Nov. 29, 1989

[30] Foreign Application Priority Data

Nov. 29, 1988 [JP] Japan .................................. 63-302009

[51] Int. Cl.⁵ .......................... B01D 3/00; C07C 51/42
[52] U.S. Cl. ..................................... 203/99; 159/47.1; 159/DIG. 23; 562/513; 562/515; 562/608
[58] Field of Search ............................. 203/99, 43, 91; 159/47.1, DIG. 23; 562/513, 515, 608

[56] References Cited

U.S. PATENT DOCUMENTS

| | | | |
|---|---|---|---|
| 736,959 | 8/1903 | Glock | 562/608 |
| 1,697,738 | 1/1929 | Suida | 562/608 |
| 1,884,241 | 10/1932 | Ricard et al. | 562/608 |
| 2,859,154 | 11/1958 | Othmer | 562/513 |
| 4,051,250 | 9/1977 | Dahm et al. | 514/369 |
| 4,052,441 | 10/1977 | Brunner | 562/513 |
| 4,483,862 | 11/1984 | Richardson et al. | 514/383 |

FOREIGN PATENT DOCUMENTS

| | | | |
|---|---|---|---|
| 0466155 | 6/1950 | Canada | 562/608 |
| 0476877 | 9/1951 | Canada | 562/608 |
| 0241590 | 12/1986 | Fed. Rep. of Germany | 562/608 |

*Primary Examiner*—Virginia Manoharan
*Attorney, Agent, or Firm*—Wenderoth, Lind & Ponack

[57] ABSTRACT

A method of manufacturing a material for medical and pharmaceutical products from pyroligneous acid extracted as water content in smoke generated by baking arbor and bark. Pyroligneous acid is heated, and resultant evaporation gas in a temperature range 98° to 103° C. is extracted and liquified by cooling.

1 Claim, No Drawings

METHOD OF MANUFACTURING MATERIAL FOR MEDICAL AND PHARMACEUTICAL PRODUCTS FROM PYROLIGNEOUS ACID

BACKGROUND OF THE INVENTION

1. Field of the Invention

This invention relates to a method of manufacturing a material for medical and pharmaceutical products from pyroligneous acid (or wood vinegar).

2. Description of the Prior Art

Pyroligneous acid is extracted as water content in smoke produced by heating trees and/or the bark thereof.

Such pyroligneous acid is extracted as by-product in the manufacture of charcoal, and usually it is discarded. Recently, researches and investigations concerning the utility of pyroligneous acid have been conducted, and methods for extracting pyroligneous acid have been developed.

However, no substantial utility effects of pyroligneous acid are obtained, and at present pyroligneous acid is finding insufficient applications.

It is recently recognized that pyroligneous acid is greatly effective as medicines. However, it has not yet been utilized for medicines.

SUMMARY OF THE INVENTION

The inventors conducted researches and investigations concerning the effects of pyroligneous acid as medicine and developed a method of obtaining a material for medical and pharmaceutical products from pyroligneous acid by removing noxious components thereof.

The present invention seeks to obtain a material for medical and pharmaceutical products from pyroligneous acid.

The inventors heated pyroligneous acid and found that the temperature thereof is elevated quickly up to 98° C., then slowly elevated up to 103° C. and then elevated quickly again, a three-step rise of temperature. The inventors extracted evaporation gas with a temperature range lower than 98° C. as first step, a range between 98°~103° C. as second step and a range higher than 103° C. as third step, liquified the extracted gas by cooling and examined the composition of the extract in the individual steps.

Liquid obtained by extraction in the first step greatly contained noxious components such as formaldehyde and methanol. Liquid obtained by extraction in the third step contained such noxious components as 3,4-benzpyrene. In contrast, liquid obtained by extraction in the second step did not contain the noxious components as in the liquids obtained by extraction in the first and third step. Animal experiments were conducted using the liquid obtained by extraction in the second step (extract) to find that the liquid had medical effects particularly on liver diseases and diabetes as in animal experiment results.

ANIMAL EXPERIMENT RESULTS

A. Effect of Administration of Extract on Therapy of Acute Hepatitis Due to Galactosamine Animal Used Rat Method of Experiment To rats was administrated galactosamine to induce acute hepatitis, and the extract was administrated twice a day to biochemically study the crisis suppression effect of the extract on acute hepatitis.

Measurement Items

Measurements of total bilirubin, glucose and GOT

Measurements

|  | T. Bilirubin (mg/dl) | Glucose (mg/dl) | GOT (K.U.) |
|---|---|---|---|
| Before administration | 0.36 | 95 | 111 |
| 1st day |  |  |  |
| Experiment Group | 0.56 | 122 | 1229 |
| Contrast Group | 0.83 | 111 | 1576 |
| 2nd day |  |  |  |
| Experiment Group | 3.12 | 95 | 3056 |
| Contrast Group | 4.91 | 62 | 3777 |
| 3rd day |  |  |  |
| Experiment Group | 2.99 | 106 | 1099 |
| Contrast Group | 5.14 | 75 | 1711 |

Result

When galactosamine was administrated to the rats, the GOT quickly increased in a period from 6 to 48 hours from the administration, and most rats dead in a week. With rats, to which the extract was administrated, the GOT increased but at a lower rate of increase compared to the contrast group rats. In addition, quick recovery was observed, and no rat dead.

B. Effect of Extract Administration on Alloxan Diabetes

Animal Used

Rat

Method of Experiment 45 mg/kg of alloxan was given venous administration to rats to induce alloxan diabetes, and the extract was given by adding it by 1% to drinking water for free drinking. Glucose was measured at time intervals.

Measurements

|  | Glucose (mg/dl) |
|---|---|
| Before administration | 95 |
| 1st week |  |
| Experiment Group | 348 |
| Contrast Group | 383 |
| 2nd week |  |
| Experiment Group | 336 |
| Contrast Group | 395 |
| 3rd week |  |
| Experiment Group | 195 |
| Contrast Group | 322 |

Result

By giving alloxane by venous administration to the rats, the glucose value which was about 100 mg/dl was increased to 350 to 400 mg/dl in two days, and the symptom of diabetes was shown. With the experiment rats, to which the extract was given as 1% content in drinking water, the glucose value was the same as that in the contrast group rats up to 14 days from the start of experiment, but it turned to be reduced gradually from the 15th day and was reduced to about 200 mg/dl in the 25th day, indicating an effect of the extract to improve the rise of the glucose value in the diabetes.

According to the present invention, the extract is obtained by heating pyroligneous acid, extracting the resultant evaporation gas in a temperature range of 98° to 103° C. and liquifying the extracted gas by cooling.

DETAILED DESCRIPTION OF THE PREFERRED EMBODIMENTS

Now, an embodiment of the present invention will be described in detail.

The kinds of trees as material of pyroligneous acid used according to the present invention and method of extraction of pyroligneous acid from trees or the like are by no means limitative.

In this embodiment, pyroligneous acid is extracted from arber and bark or oak, shinquapin, cherry, beech, etc. In the method of extraction, the trees noted above are carbonated at a temperature of 170° to 800° C., and smoke generated by this carbonization and containing water is led to be cooled down, thereby liquifying water content contained in the smoke for extraction.

From pyroligneous acid thus extracted, tar and solid impurities are separated by precitation by leading the acid for a couple of months or subjecting the acid to centrifugal separation. The supernatant liquid is taken out for use.

The supernatant liquid was heated by using a mantle heater, evaporation was from the supernatant liquid was discharged until a temperature of 98° C. is reached by the liquid, and evaporation gas generated while the supernatant liquid is being elevated in temperature from 98° to 103° C., i.e., evaporation gas in a temperature range of 98° to 103° C., is extracted, and the extracted gas is liquified by cooling.

The liquid thus obtained can be a material for medical and pharmaceutical products.

In the above method, the evaporation gas is not extracted but discharged until reaching of 98° C. by the pyroligneous acid supernatant liquid. Thus, noxious components contained in the evaporation gas can be removed. In addition, the extraction is stopped when the supernatant liquid temperature exceeds 103° C. Thus, the extract is free from noxious components contained in subsequently generated evaporation gas. It is thus possible to obtain a material for medical and pharmaceutical products, which is free from noxious components.

As has been shown, according to the present invention pyroligneous acid is heated, and evaporation gas in a temperature range of 98° to 103° C. is extracted and liquified by cooling, permitting a material for medical and pharmaceutical products free from noxious components to be obtained, which greatly contributes to the therapy of diseases. Further, since the method of manufacture is simple, the material can be obtained readily and at low cost. Further, the present invention greatly contributes to the utility of pyroligneous acid which has not heretofore been finding sufficient applications.

What is claimed is:

1. A method of manufacturing a purified pyroligneous acid for medical and pharmaceutical products from a pyroligneous acid material consisting essentially of the steps of heating trees and barks at a temperature sufficient to produce a smoke containing water in which said water comprises pyroligneous acid therein;

cooling the smoke to liquify the water containing pyroligneous acid in said smoke;

heating said pyroligneous acid; extracting resultant evaporation gas at a temperature within the range consisting of from 98° to 103° C.; and liquifying said extracted gas by cooling, such that noxious components comprising of formaldehyde, methanol and 3,4-benzyprene are avoided, and purified pyroligneous acid for medical and pharmaceutical products is obtained.

* * * * *